United States Patent [19]

Morgan

[11] Patent Number: 5,409,494
[45] Date of Patent: Apr. 25, 1995

[54] PCL ORIENTED PLACEMENT TIBIAL GUIDE

[75] Inventor: Craig D. Morgan, Greenville, Del.

[73] Assignee: Arthrex, Inc., Naples, Fla.

[21] Appl. No.: 122,308

[22] Filed: Sep. 17, 1993

Related U.S. Application Data

[62] Division of Ser. No. 837,886, Feb. 20, 1992, Pat. No. 5,269,786.

[51] Int. Cl.⁶ .............................................. A61F 5/04
[52] U.S. Cl. ....................................... 606/96; 606/88; 606/103
[58] Field of Search ..................... 606/86, 87, 88, 89, 606/96, 97, 98, 99, 102, 103, 104; 128/898; 623/13

[56] References Cited

U.S. PATENT DOCUMENTS

| | | | |
|---|---|---|---|
| 4,739,751 | 4/1988 | Sapega | 606/96 |
| 4,781,182 | 11/1988 | Purnell | 606/96 |
| 5,037,426 | 8/1991 | Goble | 606/96 |
| 5,139,520 | 8/1992 | Rosenberg | 606/87 |

*Primary Examiner*—Robert A. Hafer
*Assistant Examiner*—David J. Kenealy
*Attorney, Agent, or Firm*—Ostrolenk, Faber, Gerb & Soffen

[57] ABSTRACT

A tibial tunnel guide which enables accurate tibial tunnel placement both inside and outside the knee for use in endoscopic ACL reconstruction. The guide utilizes a consistency between the PCL and the ACL anatomic structure to accurately locate the ideal position of the tibial tunnel. The guide includes an arc shaped outrigger with a slot along its length, a sighting device secured to the outrigger in the slot and adapted to receive a guide pin, and a grasping tool adjustably secured to the outrigger in the slot having a grasper at one end. The grasper is arranged to grasp the base of the PCL near the intercondylar floor from the anteromedial portal. The sighting device is fixed relative to the position of the crotch of the grasper and locates the guide pin at an ideal position for tibial tunnel placement.

2 Claims, 2 Drawing Sheets

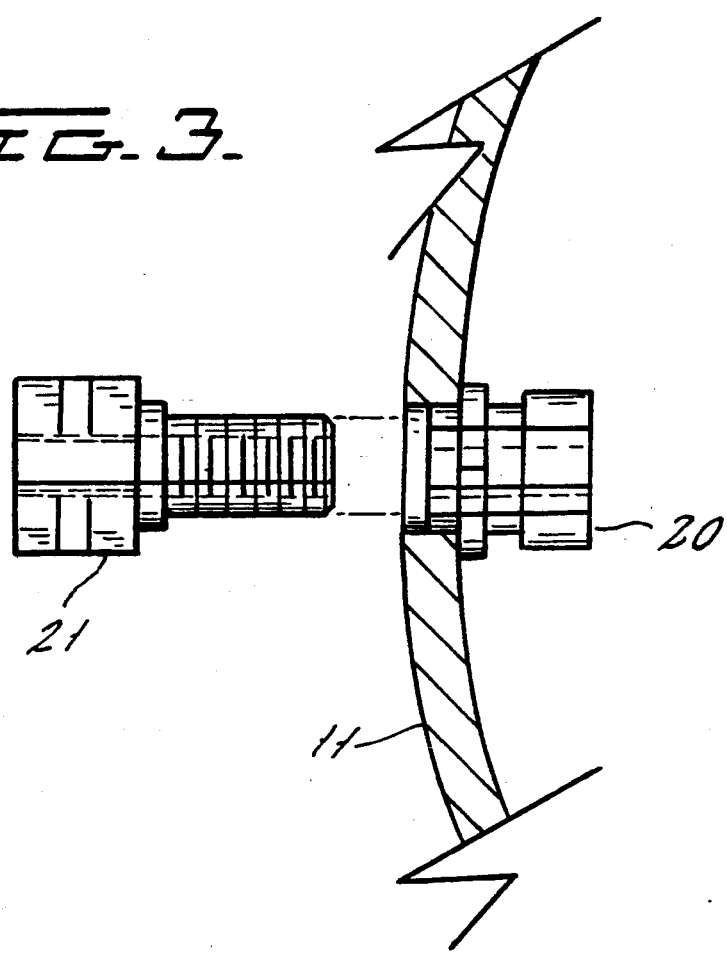
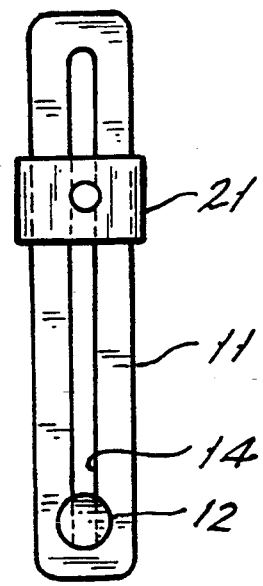

PCL ORIENTED PLACEMENT TIBIAL GUIDE

This is a division of application Ser. No. 07/837,886, filed Feb. 20, 1992, now U.S. Pat. No. 5,269,786.

BACKGROUND OF THE INVENTION

1. Field of the Invention

The present invention relates to a tibial guide for accurate tibial tunnel placement both inside and outside the knee in endoscopic ACL reconstruction.

2. Description of the Related Art

In the past, the intra-articular entry point of the tibial tunnel has tended to be placed too far anterior, resulting in roof impingement and delayed graft failure. See, e.g., S. Howell, "A Rationale for Predicting ACL Graft Inpingement by the Intercondylar Roof, A Magnetic Resonance Imaging Study", *Am. Jour. Sports Med.*, Vol. 19, No. 3, pp. 276 (1991), herein incorporated by reference. This problem has occurred largely due to the absence of any constant bony landmarks in the intercondylar notch which can be used to orient placement of guide systems for accurate reproducible tibial tunnel guide pin placement.

Also, the tibial tunnel exit point outside the knee has tended to be placed too close to the joint line. This results in a short tibial tunnel such that the tibial bone plug of a completed bone patellar tendon bone autograft reconstruction resides outside the tibial tunnel and interference screw fixation cannot be used. A second problem caused by a high tibial tunnel exit point is that the angle of the tibial tunnel in reference to the joint line is too small, which will not allow transtibial tunnel instrumentation to reach the isometric area on the lateral femoral condyle to create a femoral socket for graft fixation.

SUMMARY OF THE INVENTION

Accordingly, it is an object of the present invention to provide an apparatus and method which overcomes the above-described problems in the prior art.

The present invention achieves the foregoing objective by utilizing the anatomic structure of the knee to consistently locate the ideal location of the tibial tunnel.

The one constant anatomic structure in the intercondylar notch of the anterior cruciate ligament (ACL) deficient knee is the posterior cruciate ligament (PCL). See, e.g., C. Morgan et al., "Arthroscopic Meniscus Repair Evaluated by Second Look Arthroscopy," *Am. Jour. Sports Med.*, Vol. 19, No. 6, p. 632 (1991), herein incorporated by reference. In the intact knee, there is an important anatomic interaction between the ACL and the PCL at their midpoints, whereby the intact ACL actually wraps around or bends over the PCL in terminal extension. This dynamic interaction is an integral part of the "screw home" mechanism of the knee. Ideally, during ACL reconstruction, the entry point in the knee for the tibial tunnel should be made far enough posterior to reconstruct this important relationship between the ACL graft and the intact PCL.

The proper entry point for tibial tunnel guide pin placement resides 10 mm anterior to the leading edge of the PCL at the level of the intercondylar floor. A 10 mm diameter graft placed through a 10 mm tibial tunnel centered at this point will: 1) reach an isometric femoral socket directly in line with the tibial tunnel with the knee in 70–80 degrees of flexion; 2) avoid roof impingement in full extension with a minimal notchplasty; and 3) reconstruct the "screw home" mechanism and the interaction between the ACL graft and the intact PCL. These concepts form the basis for the present invention—an arthroscopic guide system for tibial tunnel placement oriented by the position of the posterior cruciate ligament.

The present invention consists of an arthroscopic tool which grasps the base portion of the PCL near the intercondylar floor from an anteromedial portal and automatically positions an associated external sighting device so that it delivers a guide pin to an intra-articular entry point 10 mm proximal to the crotch of the grasping portion, and thus, 10 mm from the leading edge of the PCL at the intercondylar floor. The grasping tool and sighting device are positioned relative to each other by an arc shaped outrigger. The outrigger includes a slot along its length in which the grasping tool is slidably mounted and the sighting device is fixedly mounted. The sighting device is adapted to receive a guide pin which marks the proper entry point into the knee for drilling of the tibial tunnel.

The grasping tool includes a scissor type ratchet grip, a shaft, and a grasper disposed at the end of the shaft. The grasper is closed by squeezing the scissor grip together and locked in its closed position around the PCL by a ratchet member between two finger holes on the grip. The shaft and the scissor grip are secured in the slot of the outrigger by a screw and nut arrangement. In an alternate embodiment, the grasping tool is fixedly mounted to the outrigger and the position of the sighting device is slidably mounted to the outrigger.

The method of the present invention includes the steps of inserting the grasper into the knee, grasping a base portion of the posterior cruciate ligament (PCL) near the intercondylar floor with the grasper, sliding the grasping tool along the slot of the outrigger until the sighting device points to a location 1 cm above the superior border of the pes anserinus insertion on the tibia, locking the position of the outrigger, advancing the sighting device towards the knee until it is directly adjacent the knee, inserting a guide pin into the sighting device, drilling the guide pin into the knee, and removing the apparatus, thereby leaving the guide pin in position for drilling the tibial tunnel, the guide pin being automatically positioned at an intra-articular entry point disposed 10 mm from the leading edge of the posterior cruciate ligament at the intercondylar floor.

In an alternate embodiment, the grasping tool is fixed to the outrigger and the sighting device is slid along the slot of the outrigger until the sighting device points to the location 1 cm above the superior border of the pes anserinus insertion on the tibia.

The guide of the present invention is advantageously designed such that, when the grasper is placed around the base of the PCL, the intra-articular guide pin entry point will always be 10 mm anterior to the leading edge of the PCL. By basing the outside tibial tunnel entry point on the pes anserinus insertion (i.e., 1 cm above the superior border of the pes anserinus insertion), variable anatomy regarding patellar tendon length is accommodated and the tibial tunnel is made at the proper angle such that the tunnel will be of proper length to use interference screw fixation.

BRIEF DESCRIPTION OF THE DRAWINGS

Other features and advantages of the present invention will become apparent from the following descrip

FIG. 3 shows the screw and nut attachment of the grasping tool to the outrigger.

FIG. 4 is an end view of the outrigger of the present invention.

DETAILED DESCRIPTION OF THE PREFERRED EMBODIMENT

Figure 1:
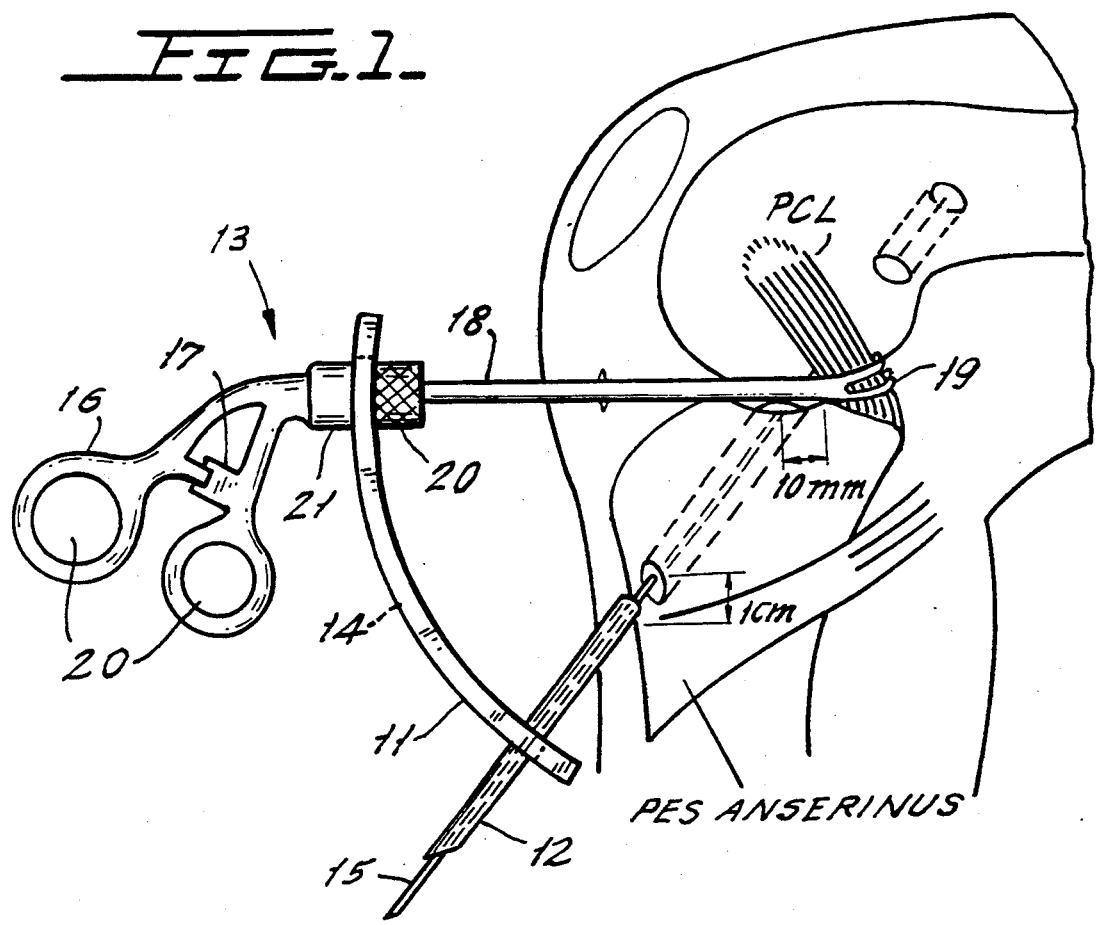
- FIG. 1 shows the apparatus of the invention in the final position after location of the tibial tunnel.

Referring to FIG. 1, the present invention is a tibial guide which utilizes the consistent anatomy of the posterior cruciate ligament (PCL) and the anterior cruciate ligament (ACL) to accurately locate the proper position of a tibial tunnel both inside and outside the knee for use in endoscopic ACL reconstruction.

The apparatus basically consists of an outrigger 11, a sighting device 12, and a grasping tool 13. The outrigger 11 is arc shaped and includes a slot 14 along its length. The slot 14 is adapted to receive the sighting device 12 and the grasping tool 13. In a preferred embodiment, the grasping tool 13 is slidably arranged in the slot 14 and the sighting device 12 is fixed in the slot 25 by a set screw. The slot 14 and grasping tool 13 are machine grooved to provide for smooth sliding of the grasping tool 13 in the slot 14. In an alternate embodiment, the grasping tool 13 is fixed in the slot 14 and the sighting device 12 is slidably arranged in the slot.

The sighting device 12 is adapted to receive a guide pin 15 which marks the proper location for the tibial tunnel. Sighting device 12 is arranged to be advanced towards the knee into engagement with the skin after it has been properly positioned and prior to insertion of the guide pin. Due to the arcuate shape of outrigger 11, sighting device 12 always locates the guide pin 15 at a position 10 mm anterior to the leading edge of the PCL at the intercondylar floor.

Figure 2:
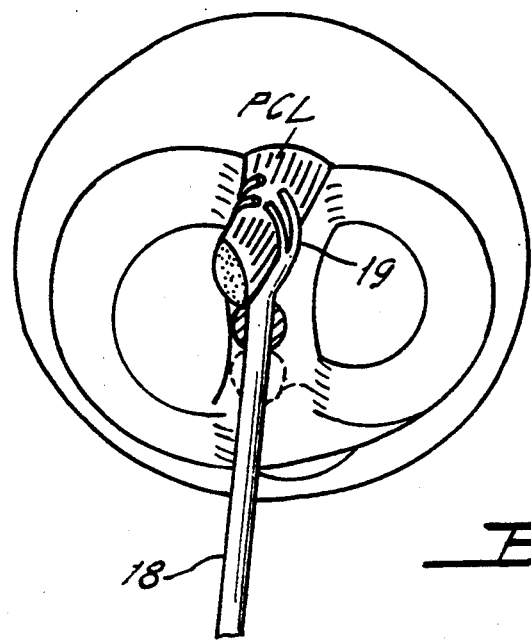
FIG. 2 shows a top view of the grasper on the PCL.

Grasping tool 13 includes a scissor grip 16 at one end and a grasper 19 at the opposite end connected by a shaft 18. The grasper is closed by squeezing the scissor grip 16 and locked in its closed position by a ratchet 17 disposed between two finger holes 20 of scissor grip 16. The grasper 19 closes through a conventional pin and hinge arrangement (not shown), and, as shown in FIG. 2, is adapted to grasp the base of the PCL near the intercondylar floor. The other end of shaft 18 is releasibly secured to the scissor grip 16 by a nut member 20. The nut member 20 is disposed on the knee side of the outrigger 11 and engages a corresponding screw member 21 disposed on the opposite side of the outrigger 11. The screw member 21 is integral with the scissor grip 16. When nut member 20 is loosened by counter-clockwise rotation, grasping tool 13 is free to slide along the slot 14 of the outrigger 11.

The method of the invention will now be described in conjunction with FIGS. 1 and 2. First, the appropriate marking hook 30 is chosen and inserted into the knee with the damaged ACL. The outrigger 10 is then slid relative to the marking hook 30 (via slot 14) until the sighting device 20, which is locked with the outrigger 11, points to a location 1 cm above the superior border of the pes anserinus insertion on the tibia. The outrigger 10 is then locked in this position by tightening screw member 54. Next, the sighting device 20 is advanced towards the knee to a position directly adjacent the skin by actuating trigger 15. A guide pin 40 is then inserted into the sighting device and drilled into the knee. At this point, the guide is removed, leaving the guide pin 40 in position so that a cannulated drill may be placed over the guide pin 40 for drilling of the tibial tunnel.

This method is consistently accurate amongst various anatomical sizes. The guide utilizes the only constant structure in the knee, i.e. the relationship between the PCL and the ACL, to position the guide pin such that the intra-articular guide pin entry point will always be 7 mm anterior to the leading edge of the PCL. Variable anatomy is accommodated by basing the outside tibial tunnel entry point on the pes anserinus insertion (i.e., 1 cm above the superior border of the pes anserinus insertion), and the tibial tunnel is made at the proper angle such that it will be of proper length for interference screw insertion. The resultant tibial tunnel is also properly angled for drilling a femoral tunnel directly in line with the tibial tunnel.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A method of accurately marking a location for a tibial tunnel for arthroscopic anterior cruciate ligament reconstruction by referencing a base of a posterior cruciate ligament at an intercondylar floor, comprising the steps of:

inserting a referencing means into a knee cavity;

positioning the inserted referencing means so as to contact the base of the posterior cruciate ligament near the intercondylar floor;

marking said tibial tunnel location with a guide pin, the guide pin being positioned in correspondence with the location of the referencing means such that the tibial tunnel is located by the guide pin at a predetermined distance from the base of the posterior cruciate ligament at the intercondylar floor when the referencing means is in contact with the base of the posterior cruciate ligament.

2. A method of marking a proper location of a tibial tunnel for arthroscopic anterior cruciate ligament reconstruction as recited in claim 1, wherein said predetermined distance is 10 mm.

* * * * *